(12) United States Patent
Arce Vera et al.

(10) Patent No.: US 9,693,942 B2
(45) Date of Patent: Jul. 4, 2017

(54) 4-OXO-2-PENTENOIC ACID AND SKIN PIGMENTATION

(71) Applicant: NESTEC S.A., Vevey (CH)

(72) Inventors: Francia Jacqueline Arce Vera, Lausanne (CH); Bertrand Bourqui, Murist (CH); Timo Buetler, Zurich (CH); Stephane Duboux, St-Prex (CH); Francis Foata, Lausanne (CH); Marjorie Guitard, Savigny (CH); Philippe Alexandre Guy, Lucens (CH); Nicolas Page, Lausanne (CH); Serge Andre Dominique Rezzi, Semsales (CH)

(73) Assignee: Nestec S.A., Vevey (CH)

(*) Notice: Subject to any disclaimer, the term of this patent is extended or adjusted under 35 U.S.C. 154(b) by 0 days.

(21) Appl. No.: 14/389,429

(22) PCT Filed: Mar. 25, 2013

(86) PCT No.: PCT/EP2013/056257
§ 371 (c)(1),
(2) Date: Sep. 30, 2014

(87) PCT Pub. No.: WO2013/144079
PCT Pub. Date: Oct. 3, 2013

(65) Prior Publication Data
US 2015/0064127 A1    Mar. 5, 2015

(30) Foreign Application Priority Data
Mar. 30, 2012 (EP) .................................... 12162361

(51) Int. Cl.
| | | |
|---|---|---|
| *A61K 8/365* | (2006.01) | |
| *A61Q 19/02* | (2006.01) | |
| *A61K 31/19* | (2006.01) | |
| *A23L 1/30* | (2006.01) | |
| *A61K 8/99* | (2017.01) | |
| *A23K 1/16* | (2006.01) | |
| *A23L 2/52* | (2006.01) | |
| *A23K 20/105* | (2016.01) | |
| *A23L 33/10* | (2016.01) | |
| *A23L 33/135* | (2016.01) | |

(52) U.S. Cl.
CPC ............ *A61K 8/365* (2013.01); *A23K 20/105* (2016.05); *A23L 2/52* (2013.01); *A23L 33/10* (2016.08); *A23L 33/135* (2016.08); *A61K 8/99* (2013.01); *A61K 31/19* (2013.01); *A61Q 19/02* (2013.01); *A23V 2002/00* (2013.01); *A23Y 2300/29* (2013.01); *A61K 2800/40* (2013.01); *A61K 2800/92* (2013.01)

(58) Field of Classification Search
None
See application file for complete search history.

(56) References Cited

U.S. PATENT DOCUMENTS

| | | |
|---|---|---|
| 4,154,817 A | 5/1979 | Tsuchiya et al. |
| 2009/0215887 A1 | 8/2009 | Wempe et al. |
| 2010/0022461 A1* | 1/2010 | Cho et al. ........................ 514/23 |

FOREIGN PATENT DOCUMENTS

WO        9313076        7/1993

OTHER PUBLICATIONS

Kakinuma et al. "Structure-Activity Relationship and Design of an Antimutagen Against the UV-Induced Mutation of *Escherichia coli*" Agric. Biol. Chem., 1986, vol. 50, No. 3, pp. 625-631.

* cited by examiner

Primary Examiner — David J Blanchard
Assistant Examiner — Sarah Chickos
(74) Attorney, Agent, or Firm — K&L Gates LLP

(57) ABSTRACT

The present invention relates generally to the field of enhancing skin appearance. One aspect of the invention aims to provide a composition comprising 4-oxo-2-pentenoic acid for use in the reduction or prevention of regions of the skin with darker pigmentation. The present invention also relates to cosmetic use of a composition comprising 4-oxo-2-pentenoic acid for the reduction or prevention of regions of the skin with darker pigmentation.

18 Claims, 3 Drawing Sheets

4-OXO-2-PENTENOIC ACID AND SKIN PIGMENTATION

CROSS REFERENCE TO RELATED APPLICATIONS

The present application is a National Stage of International Application No. PCT/EP2013/056257, filed on Mar. 25, 2013, which claims priority to European Patent Application No. 12162361.5, filed Mar. 30, 2012, the entire contents of which are being incorporated herein by reference.

The present invention relates generally to the field of enhancing skin appearance. One aspect of the invention aims to provide a composition comprising 4-oxo-2-pentenoic acid for use in the reduction or prevention of regions of the skin with darker pigmentation. The present invention also relates to cosmetic use of a composition comprising 4-oxo-2-pentenoic acid for the reduction or prevention of regions of the skin with darker pigmentation.

The skin is the largest organ of the human body. It is our first line of defense against the environment, protecting the body against pathogenic micro-organisms and preventing excessive water loss. Because of its structural organization and the wide variety of cells it is made of, the skin ensures a large spectrum of biological functions including wound healing, immune response, body temperature regulation and vitamin D production. The skin is also involved in sun protection through melanocyte cells which produce melanin, a brown pigment in the skin.

Skin color is primarily determined by the amount and type of melanin. Lower amounts of melanin result in lighter skin color while higher amounts result in darker skin color. Hyperpigmentation in the skin is caused by the over-expression or accumulation of melanin in the skin. As a result, the pathway involved in melanin production has been the target for many inhibitors so as to reduce the levels produced. One of the principal enzymes involved in the melanin pathway is tyrosinase, which catalyzes the production of melanin from tyrosine by oxidation.

The synthesis of melanin is a process under hormonal control, including the melanocyte stimulating hormone and adrenocorticotropic hormone peptides that are produced from the precursor pro-opiomelanocortin. It is also stimulated by UVB-radiation through transcriptomic regulation of tyrosinase.

The ability to modify the expression of pigment content in the skin, to promote an even skin tone or lighter skin tone, is highly desired in many societies today. A common concern relates to regions of skin having pigmentation which does not match the surrounding skin, for example moles, birthmarks, freckles, age spots or vitiligo. Other people wish to reduce skin darkening caused by exposure to the sun. To meet these needs, many attempts have been made to develop compositions which reduce or prevent skin pigmentation, but the compositions developed until now tend to have low efficiency, undesirable side effects or both. A review of the different agents known to cause hypopigmentation (loss of skin color) has been published (F. Solano et al., Pigment Cell Research, 19, 550-571 (2006)).

For over fifty years it has been known that hydroquinone reduces pigmentation when applied to the skin. Hydroquinone inhibits the production of melanin by, among other things, inhibiting the action of tyrosinase. Unfortunately, hydroquinone may have disadvantages due to its cytotoxicity and side effects such as skin irritation. Hydroquinone is banned in a number of countries for general cosmetics purposes.

Other external preparations intended to reduce skin pigmentation have included kojic acid, ascorbic acid, hydrogen peroxide, colloidal sulphur and monobenzone. Monobenzone is the monobenzyl ether of hydroquinone. However, these agents are undesirable due to possible stability and/or safety problems. Kojic acid, like hydroquinone, is a tyrosinase inhibitor but also may have undesirable side effects such as allergy and skin irritation and often is unstable in cosmetics formulations. Ascorbic acid, which is sometimes used for preventing or reducing pigmentation, may be easily oxidized and often is unstable in compositions with high water-content such as cosmetics. Ascorbic acid may also cause adverse effects as it can induce a large increase in free radicals when in the presence of traces of metal ions. Hydrogen peroxide solutions may have problems of preservation stability and safety. Colloidal sulphur has an unusual odor and may be difficult to use as a component of skin-lightening agents. Monobenzone may cause the destruction of melanocytes and permanent depigmentation. Monobenzyl is not recommended for skin conditions other than vitiligo.

Topical retinoid and topical corticosteroids have been suggested as hypo-pigmenting agents, as have laser treatment and chemical peels, but these often fall short of desirable responses. Skin lightening compositions having an acetylcholinesterase inhibitor have been described in WO2010/066639.

Natural materials have been used for centuries in Asia and Europe in attempts to bleach skin or to enhance the appearance of fair skin. These include the use of lemon, orange, cucumber, ginkgo, carob, rose fruit, geranium herb, cinnamon, sweet marjoram and rosemary.

To combat disorders related to abnormal pigmentation or to lighten skin tone various compounds have been proposed which reduce tyrosinase activity when applied topically to the skin. Unfortunately, the treatments currently available are not entirely satisfactory, in particular in terms of side effects such as skin irritation which may occur with certain topical agents.

It would thus be highly desirable to have additional compositions available that reduce or prevent regions of the skin with darker pigmentation without the drawbacks of some of the prior art, and in order to broaden the range of treatment options available and so enhance choice and adaptation to personal needs. In particular, it would be desirable to find an effective composition whose active ingredient is obtained from a natural source.

The object of the present invention is to improve the state of the art and in particular to provide a composition for use in the reduction or prevention of regions of the skin with darker pigmentation, overcoming at least some of the disadvantages described above.

The inventors were surprised to see that the object of the present invention could be achieved by the subject matter of the independent claims. The dependent claims further develop the idea of the present invention.

It has been surprisingly found by the inventors that 4-oxo-2-pentenoic acid effectively suppresses the production of melanin. The inventors also found that the production of tyrosinase, an enzyme involved in the first step of melanin synthesis, is decreased by 4-oxo-2-pentenoic acid.

The inventors were also surprised to find that 4-oxo-2-pentenoic acid was obtainable from some bacterial strains. For example, bacterial preparations of *Bifidobacterium* breve CNCM I-3865 and *Bifidobacterium breve* ATCC 15700™ both yielded 4-oxo-2-pentenoic acid when heated for 6 hours at 90° C. 4-oxo-2-pentenoic acid was found to be in the soluble fraction after centrifuging and filtering the heat treated bacterial preparations.

*Bifidobacterium breve* CNCM I-3865 was deposited with the COLLECTION NATIONALE DE CULTURES DE MICROORGANISMES (CNCM), INSTITUT PASTEUR, 25 rue du Docteur Roux, F-75724 PARIS Cedex 15, France, on Nov. 15, 2007.

*Bifidobacterium breve* ATCC 15700™ can be obtained commercially, e.g., from the American type Culture Collection (ATCC), Manassas, Va., USA, under the trademark ATCC 15700.

Consequently, the present invention relates in part to a composition comprising 4-oxo-2-pentenoic acid for use in the reduction or prevention of regions of the skin with darker pigmentation.

The present invention also relates to the use of 4-oxo-2-pentenoic acid in the preparation of a composition for the reduction or prevention of regions of the skin with darker pigmentation.

Regions of skin with dark pigmentation may result from injury or inflammation related skin conditions, cuts, burns or acne breakouts, and reducing darker skin pigmentation may therefore be considered a restoring step of a therapeutic measure.

Dark pigmentation of the skin is usually the result of the accumulation of melanin in localized areas—a condition named hyperpigmentation. Hyperpigmentation is associated with a number of diseases including Addison's disease, Cushing's disease, acanthosis nigricans, thyroid disease and melasma. Preventing hyperpigmentation is therefore a prophylactic application of the present invention.

Consequently, the composition of the present invention may be for a therapeutic use. The composition comprising 4-oxo-2-pentenoic acid may be for use in the reduction or prevention of regions of the skin with darker pigmentation resulting from conditions selected from the group consisting of piebaldism, vitiligo, injury or inflammation related skin conditions, Addison's disease, Cushing's disease, acanthosis nigricans and thyroid disease. Vitiligo is a condition that causes depigmentation of sections of skin. In cases of vitiligo, the regions of the skin with darker pigmentation according to the invention may be the unaffected areas.

4-oxo-2-pentenoic acid has the CAS number 4743-82-2 and the following formula:

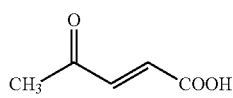

"Reduction of regions of the skin with darker pigmentation" is understood to mean a reduction in the total area of the regions of the skin with darker pigmentation and/or a reduction in the number of regions of the skin with darker pigmentation and/or a reduction in the darkness of pigmentation of those regions of the skin. "Prevention of regions of the skin with darker pigmentation" is understood to include complete or partial prevention of formation of regions of the skin with darker pigmentation. The regions of the skin are not limited in size and may extend over the whole body surface.

The present invention also provides non-therapeutic use of a composition comprising 4-oxo-2-pentenoic acid. One embodiment of the invention may be cosmetic use of a composition comprising 4-oxo-2-pentenoic acid for the reduction or prevention of regions of the skin with darker pigmentation.

The invention may provide cosmetic use of 4-oxo-2-pentenoic acid in skin lightening. Skin lightening is the act of reducing the overall degree of skin pigmentation in regions of the skin. Skin lightening may be considered desirable by some people in order to reverse the effects of sun exposure or to follow fashions for lighter skin which occur in certain cultures.

The invention may further provide cosmetic use of 4-oxo-2-pentenoic acid in the reduction or prevention of regions of the skin with darker pigmentation wherein the regions of the skin with darker pigmentation are selected from the group consisting of moles, birthmarks, melasma, freckles, age spots or combinations thereof. This is advantageous as a homogeneous complexion free of skin pigment imperfections is considered aesthetically desirable by many people.

In the present invention the 4-oxo-2-pentenoic acid may be obtainable, for example obtained, from natural sources. Many people are concerned about the safety of materials industrially synthesized from chemical feedstock, especially when these materials are to be ingested and prefer materials obtained from natural sources.

Surprisingly, the inventors found that some strains of bacteria provide a natural source of 4-oxo-2-pentenoic acid. In particular, the inventors have found that 4-oxo-2-pentenoic acid can be obtained from *Bifidobacterium breve* CNCM I-3865 or *Bifidobacterium breve* ATCC 15700™ (the type strain for *Bifidobacterium breve*). It is particularly advantageous to use bacteria as a source of 4-oxo-2-pentenoic acid as the production of large quantities of 4-oxo-2-pentenoic acid is feasible, for example using bioreactors. Accordingly, in the present invention the 4-oxo-2-pentenoic acid may be obtainable, for example obtained, from *Bifidobacterium breve* CNCM I-3865 or *Bifidobacterium breve* ATCC 15700™.

The bacteria may be heat treated at about 60-180° C., preferably at about 80-160° C., for example at about 110-150° C. in commercial production processes. The inventors found that heat treatment at these temperatures provided a satisfactory yield of 4-oxo-2-pentenoic acid within an acceptable time. Without wishing to be bound by theory it is understood that increasing the temperature of heat treatment increases the rate of formation of 4-oxo-2-pentenoic acid but also increases the rate of its degradation. Accordingly these temperatures give a good balance between the rate of formation of 4-oxo-2-pentenoic acid and its degradation.

Typical compositions comprising 4-oxo-2-pentenoic acid may comprise 4-oxo-2-pentenoic acid in an amount of at least 1 mg/kg of the composition. Generally, it is preferred if the composition comprises 4-oxo-2-pentenoic acid in an amount of at least 10 mg/kg of the composition, for example between 50 mg and 50 g per kg of the composition.

The optimum amount of 4-oxo-2-pentenoic acid to be administered can be easily determined by skilled artisans.

In therapeutic applications, compositions are administered in an amount sufficient to at least partially cure or arrest the symptoms of a disorder and/or its complications. An amount adequate to accomplish this is defined as "a therapeutic effective dose". Amounts effective for this purpose will depend on a number of factors known to those of skill in the art such as the severity of the disorder and the weight and general state of the patient.

In prophylactic applications, compositions according to the invention are administered to a patient susceptible to or otherwise at risk of a particular disorder in an amount that is sufficient to at least partially reduce the risk of developing a disorder. Such an amount is defined to be "a prophylactic effective dose". Again, the precise amounts depend on a number of patient specific factors such as the patient's state of health and weight.

For cosmetic use, compositions according to the invention are administered to a person in an amount sufficient to at least partially reduce a visible or tangible imperfection of a physical appearance of a person. Such an amount is defined to be "a cosmetic effective dose". Again, the precise amounts depend on a number of person specific factors such as the person's gender, race, complexion, age, or state of health.

Generally, the compositions of the present invention may be administered in a therapeutic effective dose, a prophylactic effective dose or a cosmetic effective dose.

The composition of the present invention may be administered in a daily dose corresponding to between 2 µg and 20 mg of 4-oxo-2-pentenoic acid per kg of body weight, preferably between 20 µg and 2 mg of 4-oxo-2-pentenoic acid per kg of body weight, for example between 40 µg and 1 mg of 4-oxo-2-pentenoic acid per kg of body weight.

It can be advantageous to target specific areas of the skin to reduce pigmentation, for example a freckle or age spot where the aim is to match the colour of the surrounding skin area. A topical application of the composition allows such a targeted delivery. Accordingly, in the present invention, the composition may be administered topically.

Compositions according to the present invention are also orally administrable. This has the advantage of the composition acting globally on the entire skin by means of a rapid and relatively non-restrictive mode of administration.

Regions of the skin with darker pigmentation can affect animals as well as humans. It is therefore an advantage to provide a composition to be administered to humans, pets or livestock. It can improve owner satisfaction for their pet to be aesthetically pleasing and imperfections in skin pigmentation can limit the success of animals in competitive exhibitions and reduce their perceived value. The present invention provides a composition which may be administered to humans, pets or livestock.

4-oxo-2-pentenoic acid and the composition described in the present invention may be administered to adults and/or to the elderly.

A subject is considered adult if they are of relatively mature age. Typically subjects are considered adult when they are sexually mature and capable of reproduction.

A subject is considered as "elderly" if they have surpassed the first two thirds of their average expected lifespan in their country of origin, preferably if they have surpassed the first three quarters of the average expected lifespan in their country of origin, more preferably if they have surpassed the first four fifths of the average expected lifespan in their country of origin. For example, a human male born in the UK in 2010 has a life expectancy at birth of 78 years according to the UK Office of National Statistics, therefore they would be considered elderly at ages over 52 years, preferably over 58 years 6 months and more preferably over 62 years 5 months. For pets and livestock the species and breed should be taken into account. For example a Yorkshire Terrier dog has a life expectancy of about 12 years (E. J. Taylor et al., Proceedings of the Nutrition Society, 54, 645-656 (1995)) and so would be considered elderly at ages over 8 years, preferably over 9 years and more preferably over 9 years 7 months.

The occurrence of regions of the skin with darker pigmentation such as age spots (solar lentigines), sun spots, liver spots, and melasma (also known as chloasma) is often due to long-term exposure to ultra-violet radiation from sunlight or sunbeds. People who have been alive longer are more likely to have had longer exposure to ultraviolet light. A composition of the present invention may be administered to adults, and/or the elderly.

The nature of the composition is not particularly limited. The composition for use in the reduction or prevention of regions of the skin with darker pigmentation may be selected from the group consisting of a food composition, a pharmaceutical composition, a food additive, a nutraceutical, a drink, a pet food composition, a powder, a cream, a lotion or a gel. A nutraceutical is a food stuff (as a fortified food, oral supplement or dietary supplement) that provides health benefits. The composition according to the invention may be in any of the galenical forms normally available for the method of administration selected. The carrier may be of diverse nature depending on the type of composition under consideration.

The composition for cosmetic use may be selected from the group consisting of a food composition, a food additive, a drink, a pet food composition, a cosmetic composition, a powder, a cream, a lotion or a gel.

Food compositions according to the present invention are diverse in character, for example: milk, yogurt, cheese, fermented milks, milk-based fermented products, ice-creams, cereal-based products or fermented cereal-based products, milk-based powders, chilled or shelf stable beverages, confectionery, animal feed, in particular for domestic animals.

The food composition may also further comprise a protein source, a carbohydrate source, a lipid source, a mineral source and/or a vitamin source. The presence of proteins, carbohydrates, lipids, minerals and/or vitamins may have several advantages. These compounds generally contribute to the taste and mouthfeel of the final product and provide the body with beneficial nutrients. They also allow formulating the composition of the present invention as a complete nutritional formula, so that no additional nutrition is needed.

Compounds soluble in water have the advantage of being conveniently administered in a number of ways, including orally as solutions, or in capsules or tablets, by inhalation, in aqueous gels or creams for topical application, in bath soaks, shower gel or shampoo, or as eye-drops, nose-drops or ear-drops. The composition comprising 4-oxo-2-pentenoic acid may be water-based, for example the composition may comprise 4-oxo-2-pentenoic acid dissolved in water.

Those skilled in the art will understand that they can freely combine all features of the present invention disclosed herein. In particular, features described for different embodiments of the present invention may be combined. For example, features described for composition for a therapeutic use may be combined with the features described for the cosmetic use of the present invention and vice versa. Further advantages and features of the present invention are apparent from the following figures and non-limiting examples.

EXAMPLE 1

Effect of 4-oxo-2-Pentenoic Acid on Skin Pigmentation

In order to evaluate the effect of 4-oxo-2-pentenoic acid on skin pigmentation the inventors used a culture of murine melanocytes (B16) and performed 2 tests: assessment of melanin production and assessment of tyrosinase production.

Cell Culture Conditions.

B16 cells were cultured in DMEM 1 g/L glucose without phenol red supplemented with 10% foetal calf serum, in a humidified chamber at 37° C. and containing 5% CO2. (DMEM is Dulbecco's Modified Eagle Medium.)

Production of Melanin by B16 Murine Melanocyte Cell Line.

Cells were incubated for 72 hours with 4-oxo-2-pentenoic acid at a concentration of 7 µM or a test reference of kojic acid (a known inhibitor of melanin production) at 400 µg/mL. This was performed in the presence or absence of NDP-MSH, an analog of MSH (melanocyte-stimulating hormone). The total quantity of melanin (extracellular and intracellular) was evaluated by measuring the optical density at 405 nm of each sample against melanin standards in the presence or absence of NDP-MSH. The control condition corresponds to a culture of B16 murine melanocytes treated just with the medium, no other compound being added.

Production of Tyrosinase by B16 Murine Melanocyte Cell Line.

Cells were incubated for 48 hours with 4-oxo-2-pentenoic acid at a concentration of 7 µM or a test reference of kojic acid at 400 µg/mL. The production of tyrosinase was evaluated by immunolabeling. The control condition corresponds to a culture of B16 murine melanocytes treated just with the medium, no other compound being added.

Figure 1:
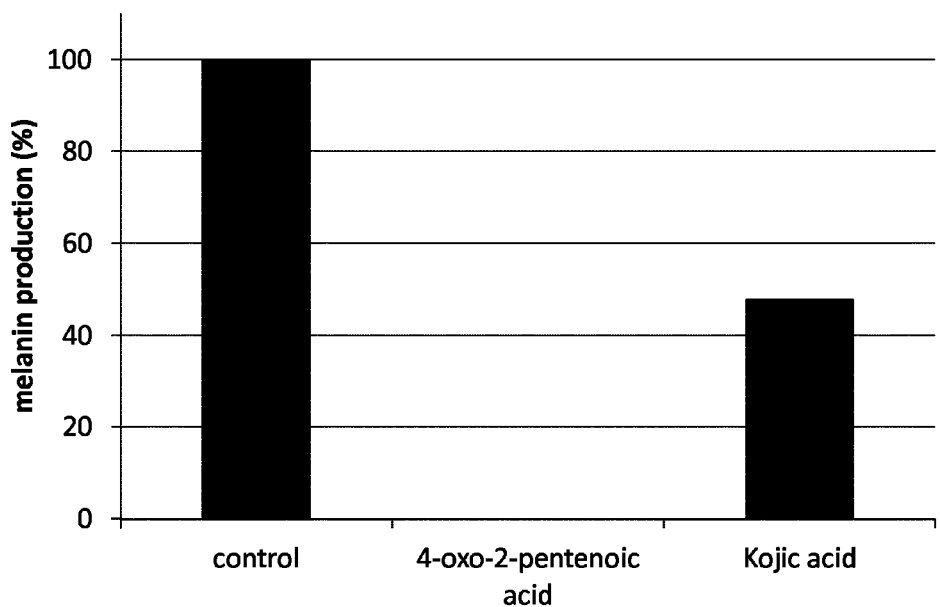
FIG. 1 shows melanin production by B16 murine melanocytes pre-treated with 4-oxo-2-pentenoic or kojic acid expressed as a percentage of the melanin produced by the control (a culture of B16 murine melanocytes with no other compound added).

Results are expressed as a percentage relative to the control. Kojic acid induced, as expected, a decrease in melanin production to 48% of that produced in the control, whereas 4-oxo-2-pentenoic acid reduced the melanin production to zero, see FIG. 1.

Figure 2:
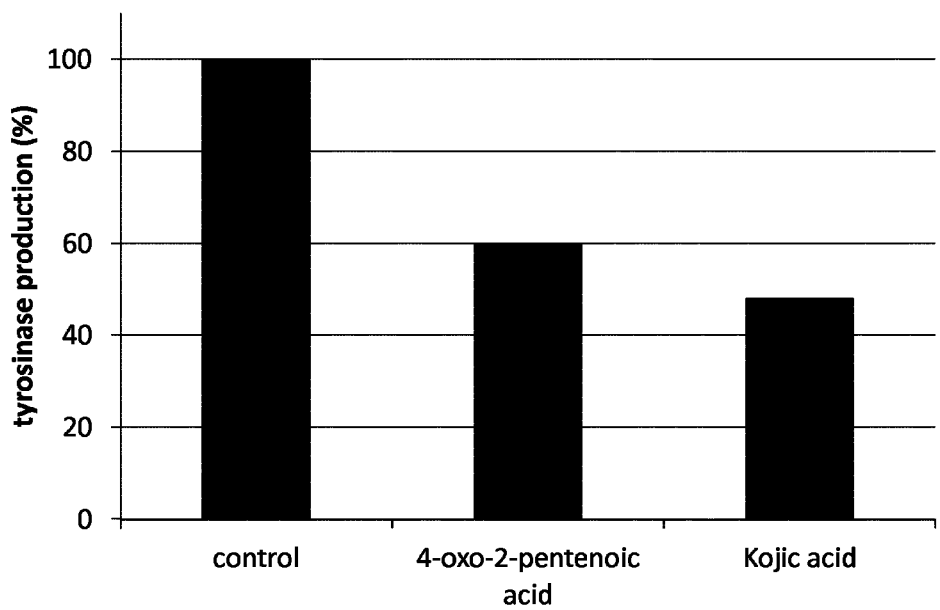
FIG. 2 shows tyrosinase production by B16 murine melanocytes pre-treated with 4-oxo-2-pentenoic or kojic acid expressed as a percentage of the tyrosinase produced by the control (a culture of B16 murine melanocytes with no other compound added).

The production of tyrosinase was also decreased by both kojic acid and 4-oxo-2-pentenoic acid (FIG. 2), suggesting that the decrease in melanin was due, at least in part, to tyrosinase inhibition. Although 4-oxo-2-pentenoic acid was more effective than kojic acid at suppressing melanin production, it was less effective at suppressing tyrosinase production which may indicate that 4-oxo-2-pentenoic acid also influences mechanisms acting upstream or downstream of this enzyme.

The presented data allows us to conclude that 4-oxo-2-pentenoic acid can be used in the reduction or prevention of regions of skin with darker pigmentation.

EXAMPLE 2

Bacterial Strains as a Source of 4-oxo-2-Pentenoic Acid

Three bacterial strains were used to investigate whether 4-oxo-2-pentenoic acid could be obtained from microorganisms: *Bifidobacterium breve* CNCM I-3865 (NCC2950), *Bifidobacterium breve* CNCM I-3914 (NCC466) and *Bifidobacterium breve* ATCC 15700™ (NCC2791). *Bifidobacterium breve* CNCM I-3914 was deposited with the COLLECTION NATIONALE DE CULTURES DE MICROORGANISMES (CNCM), INSTITUT PASTEUR, 25 rue du Docteur Roux, F-75724 PARIS Cedex 15, France, on Feb. 5, 2008.

For each strain, 10 ml of MRS agar with 0.05% cystein was inoculated with 20 µl of glycerol stock and incubated overnight at 37° C. in anaerobic condition to form pre-cultures. Further cultures were then made by inoculating 10 ml of MRS with 0.05% cystein with the pre-cultures (final $OD_{600}$ adjusted at 0.1). The cultures were incubated for 16 hours at 37° C. in anaerobic conditions to form the P2 cultures. 200 ml of MRS with 0.05% cystein was inoculated with the P2 cultures (final $OD_{600}$ adjusted at 0.1) and the bottles were incubated for 16 hours at 37° C. in anaerobic conditions.

The $OD_{600}$ was measured, the cultures were centrifuged at 3300 g for 10 min and the bacterial pellets were washed two times with cold 1×PBS (Phosphate buffered saline) and normalized to OD 50 with 1×PBS.

Bacterial fractions were obtained in two ways for each bacterial strain; a "crude preparation" and a "pure preparation".

The bacterial "crude preparations" were obtained as follows. 5 ml of the OD 50 bacterial preparations were heated for 6 hours at 90° C. in a heating block (Dri-Block DB-3 heating block from Techne, Staffordshire, United Kingdom). The heated bacterial preparations were centrifuged at 3300 g for 10 min at +4° C. and the supernatants were filtered using 0.22 µm syringe filters and stored at +4° C. until further analyses.

The bacterial "pure preparations" were obtained as follows. 5 ml of the OD 50 bacterial preparations were centrifuged at 3300 g for 10 min at +4° C. and the bacterial pellets were re-suspended with 5 ml of water. The bacterial cells were disrupted using mini bead beat (MBB) apparatus in a cold room (six cycles of 90 sec at maximum speed with 10 min of pause between each cycle). The disrupted cells were centrifuged for 1 h at 3300 g at +4° C. and the pellet was re-suspended with 5 ml of 1×PBS and heated for 6 hours at 90° C. in a heating block. The heated preparations were centrifuged for 10 min at 3300 g at +4° C. The supernatants were filtered using 0.22 µm syringe filters and stored at +4° C. until further analyses.

EXAMPLE 3

Quantification of 4-oxo-2-Pentenoic Acid by HPLC-MS/MS

In order to quantify 4-oxo-2-pentenoic acid, a high throughput analytical method involving coupling high performance liquid chromatography with electrospray ionization tandem mass spectrometry (HPLC-ESI-MS/MS) was developed.

4-oxo-2-pentenoic acid standard was purchased from Alfa Aesar (Ward Hill, USA). HPLC grade water, methanol and acetic acid were purchased from Lichrosolv (Merck, Darmstadt, Germany). HPLC vials and 2 mm inserts were purchased from Agilent (Santa Clara, Calif.). 4-oxo-2-pentenoic acid was found to be soluble in water to at least 20 mg/ml. 4-oxo-2-pentenoic acid standard compound was solubilised in water at a final stock solution of 10 mg/ml and further diluted in water to build a calibration curve.

HPLC-ESI-MS/MS analyses were carried out on a turbulent flow chromatography (TFC) system (Thermo Fisher, Waltham, Mass.) coupled to a 3200 Q TRAP mass spectrometer (Applied Biosystems). The analytical column used was a Hypersil Gold AQ (3×50 mm, 5 µm) purchased from Thermo Fisher (Waltham, Mass.) running at room temperature and a constant flow rate of 600 µl/min. The mobile phases were constituted with solvent A) water containing 0.05% acetic acid and B) methanol containing 0.05% acetic acid. The gradient program was: 0 min 0% B, held for 40 sec (0-0.67 min) at 0% B, ramping to 50% B in 180 sec (0.67-3.67 min), ramping from 50 to 90% B in 10 sec (3.67-3.83 min), held for 120 sec (5.83 min) at 90% B, before going back to 0% B and held for an additional 300 sec (5.83-10.83 min). The injection volume was 5 µl.

MS data acquisition was realized in electrospray negative ionization mode. MS tuning was performed by infusing a solution of 4-oxo-2-pentenoic acid standard (5 µg/ml in water) at a flow rate of 10 µl/min mixed with a HPLC flow of solvents A and B (80/20, v:v; 0.6 ml/min) using a T-connector. Nitrogen was used for the nebulizer and curtain gases. The interface heater was activated and the block source temperature was maintained at 700° C. with a capillary voltage set at −4.5 kV. Nitrogen was also used as collision gas at a medium pressure selection. MS/MS detection was realized using the selected reaction monitoring (SRM) acquisition mode. The two most intense fragment ions were selected by scanning m/z 113→69 (collision energy of 11 eV), and m/z 113→41 (collision energy of 26 eV), using constant dwell times of 50 ms (total scan time of 110 ms). The declustering potential was set at −29 V. Quantitative analyses were performed using the most intense SRM signal whereas the second transition was used for analyte confirmation based on appropriate area ratio calculated from standard solutions. Data processing was performed using Analyst 1.5.1 software (Applied Biosystems).

Figure 3:
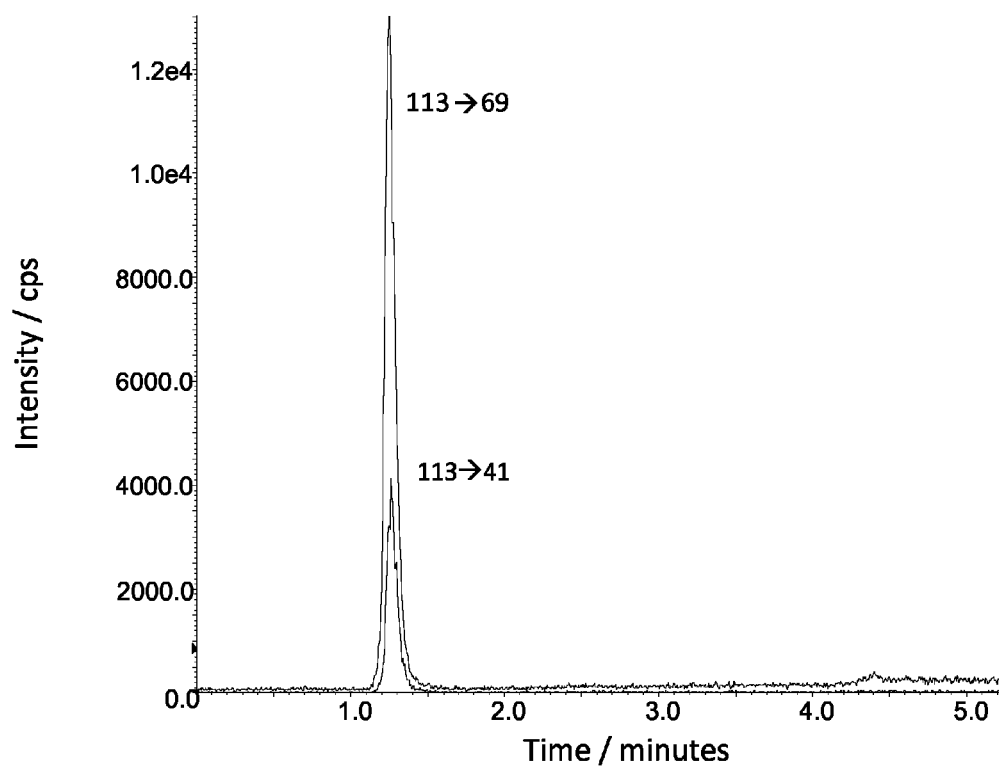
FIG. 3 shows a typical chromatogram of a 4-oxo-2-pentenoic acid standard dissolved in water. The higher SRM is associated to the transition reaction of m/z 113→69, while the lower SRM corresponds to transition reaction of m/z 113→41. The retention time is expressed in minutes (x-axis). Signal intensity (y-axis) is expressed in Cps.

Detection of 4-oxo-2-Pentenoic Acid in PBS and Water by HPLC-MS/MS:

4-oxo-2-pentenoic acid was solubilised in 1×PBS or water, and the detection by HPLC-MS/MS performed as described in the previous section. The SRM associated with the transition reaction of m/z 113→69 revealed a more intense signal than the SRM associated with the transition m/z 113→41 at a retention time of 1.25 min. Similar retention times for both transitions were observed confirming the validity of the analysis, (FIG. 3). The molecule 4-oxo-2-pentenoic acid was successfully detected in both 1×PBS (data not shown) and water (FIG. 3).

Establishment of 4-oxo-2-Pentenoic Acid Standard Curve:

In order to quantify precisely the amount of 4-oxo-2-pentenoic acid in bacterial fractions, standard curves were established for 4-oxo-2-pentenoic acid in simple matrices like 1×PBS or HPLC grade water. Commercial 4-oxo-2-pentenoic acid was suspended in 1×PBS and water at different doses. The HPLC-ESI-MS/MS method was then used to quantify the estimated doses of 4-oxo-2-pentenoic acid. Good linearity was observed between the quantity of 4-oxo-2-pentenoic acid (from 0.1 to 25 µg/ml) and the resulting intensities (expressed in cps) both in 1×PBS and HPLC grade water.

Quantification of 4-oxo-2-Pentenoic Acid in Bacterial Fractions:

4-oxo-2-pentenoic acid was quantified in the heat treated bacterial preparations described above. All samples were diluted in HPLC grade water (3 dilutions/sample) before HPLC-ESI-MS/MS analysis. The results are summarized in table A.

TABLE A

Concentrations of 4-oxo-2-pentenoic acid (µg/ml) in crude and pure bacterial heated preparations (OD 50) 6 hours of heating at 90° C. N.D stands for "Not Detectable", below the detection limit of the method.

| Strain | Strain Code | 4-oxo-2-pentenoic acid (µg/ml) Crude preparation | 4-oxo-2-pentenoic acid (µg/ml) Pure preparation |
|---|---|---|---|
| B. breve | CNCM I-3865 | 95.3 | 126.8 |
| B. breve | ATCC 15700 | 2.1 | 16.4 |
| B. breve | CNCM I-3914 | N.D. | N.D. |

EXAMPLE 4

The Influence of Heating Temperature and Time on the Production of 4-oxo-2-Pentenoic Acid from *Bifidobacterium breve* CNCM I-3865

To characterize the production of 4-oxo-2-pentenoic acid from *Bifidobacterium breve* CNCM I-3865 upon heat treatment a kinetic experiment was performed using various temperatures. The "master stock" of biomass used for this experiment was produced in bioreactors at 37° C. with MRS medium under anaerobic and pH control conditions. After the grow culture (16 h), the culture media was removed and the cells were washed two times with 1×PBS, concentrated to OD 134 (1.5E+10 cfu/ml) in 1×PBS with 10% glycerol then stored at −80° C. in 50 ml aliquots.

A "working biomass" of *Bifidobacterium breve* CNCM I-3865 was then prepared from the biomass master stock as follows: The biomass was washed two times with 1×PBS and adjusted to OD 40 in 1×PBS, which corresponds to 1 and 0.5E10 cfu/ml, respectively.

Figure 4:
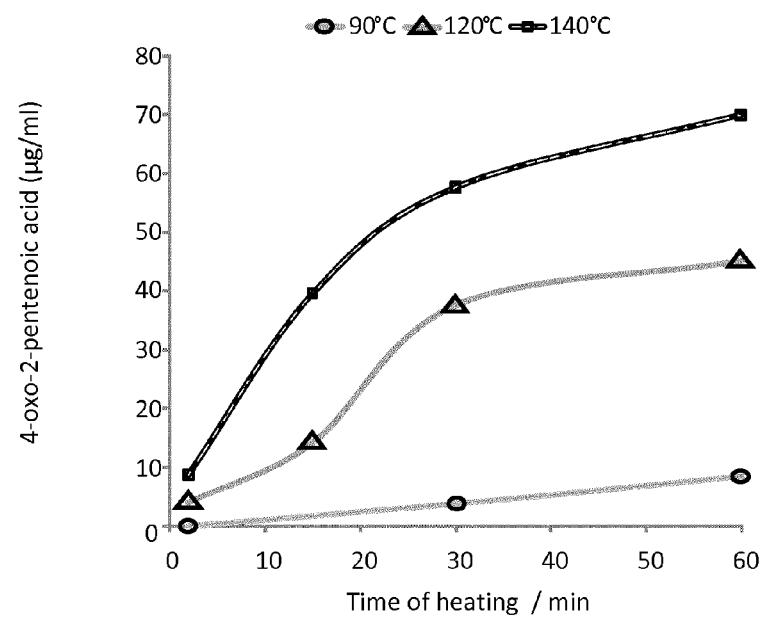
FIG. 4 shows 4-oxo-2-pentenoic acid quantification using HPLC-ESI-MS/MS of crude preparations of *Bifidobacterium breve* CNCM I-3865 (OD 40) heated for 2, 15, 30, and 60 minutes at 90° C. (indicated by circles ○), 120° C. (indicated by triangles Δ) and 140° C. (indicated by squares □).

A Temperature Heating Apparatus (THA) was used to investigate the effect of different heating times and temperatures. This system is a small scale version of typical apparatus found in production environments. Steam is used to heat up a holding tube containing cartridges of biomass. Sample temperatures of 90° C., 120° C. and 140° C. were applied for periods up to 60 minutes. 5 ml of each heat-treated biomass was then centrifuged for 10 min at 5000 g and the supernatants were filtered (0.2 µm) and the 4-oxo-2-pentenoic acid content quantified by HPLC-ESI-MS/MS. The amounts of 4-oxo-2-pentenoic acid generated are shown in FIG. 4.

The invention claimed is:

1. A method for the reduction of regions of the skin with darker pigmentation relative to the surrounding skin resulting from conditions selected from the group consisting of piebaldism, vitiligo, injury or inflammation related skin conditions, Addison's disease, Cushing's disease, acanthosis nigricans and thyroid disease, the method comprising:

administering to an individual in need of same a composition comprising a molecule consisting of 4-oxo-2-pentenoic acid.

2. The method in accordance with claim 1, wherein the 4-oxo-2-pentenoic acid is obtainable from *Bifidobacterium breve* CNCM I-3865 or *Bifidobacterium breve* ATCC 15700.

3. The method in accordance with claim 1, wherein the composition comprises 4-oxo-2-pentenoic acid in an amount of at least 1 mg per kg of the composition.

4. The method in accordance with claim 1, wherein the composition is administered in a daily dose corresponding to between 2 μg and 20 mg of 4-oxo-2-pentenoic acid per kg of body weight.

5. The method in accordance with claim 1, wherein the composition is selected from the group consisting of a food composition, a pharmaceutical composition, a food additive, a nutraceutical, a drink, a pet food composition, a powder, a cream, a lotion and a gel.

6. A method for the reduction of regions of the skin with darker pigmentation relative to the surrounding skin from increased melanin production wherein the regions of the skin with darker pigmentation are selected from the group consisting of moles, birthmarks, melasma, freckles, age spots and combinations thereof the method comprising:

providing to an individual in need of same a cosmetic comprising a molecule consisting of 4-oxo-2-pentenoic acid.

7. The method in accordance with claim 6 for skin lightening.

8. The method in accordance with claim 6, wherein the 4-oxo-2-pentenoic acid is obtained from natural sources.

9. The method in accordance with claim 6, wherein the 4-oxo-2-pentenoic acid is obtainable from *Bifidobacterium breve* CNCM I-3865 or *Bifidobacterium breve* ATCC 15700.

10. The method in accordance with claim 6, wherein the cosmetic comprises 4-oxo-2-pentenoic acid in an amount of at least 1 mg per kg of the composition.

11. The method in accordance with claim 6, wherein the cosmetic is applied in a daily dose corresponding to between 2 μg and 20 mg of 4-oxo-2-pentenoic acid per kg of body weight.

12. The method in accordance with claim 6, wherein the cosmetic is applied topically.

13. The method in accordance with claim 6, wherein the cosmetic is administered orally.

14. The method in accordance with claim 6, wherein the cosmetic is selected from the group consisting of a food composition, a food additive, a drink, a pet food composition, a cosmetic composition, a powder, a cream, a lotion and a gel.

15. A method for the reduction of regions of the skin with darker pigmentation relative to the surrounding skin from increased melanin production wherein the regions of the skin with darker pigmentation are selected from the group consisting of moles, birthmarks, melasma, freckles, age spots and combinations thereof the method comprising:

administering to an individual in need of a reduction in production of melanin a composition comprising a molecule consisting of 4-oxo-2-pentenoic acid.

16. The method in accordance with claim 15, wherein the composition is applied topically.

17. The method in accordance with claim 15, wherein the composition is administered orally.

18. The method in accordance with claim 1, wherein the composition is administered in a daily dose corresponding to between 2 μg and 20 mg of 4-oxo-2-pentenoic acid per kg of body weight.

* * * * *